(12) United States Patent
Loskutoff

(10) Patent No.: US 9,314,790 B1
(45) Date of Patent: Apr. 19, 2016

(54) SYSTEM FOR SEPARATION OF A SAMPLE

(75) Inventor: Naida M. Loskutoff, Omaha, NE (US)

(73) Assignee: Safety Art, LLC, Omaha, NE (US)

( * ) Notice: Subject to any disclaimer, the term of this patent is extended or adjusted under 35 U.S.C. 154(b) by 956 days.

(21) Appl. No.: 12/796,385

(22) Filed: Jun. 8, 2010

Related U.S. Application Data

(63) Continuation-in-part of application No. 11/827,767, filed on Jul. 13, 2007, now abandoned, which is a continuation of application No. 10/478,917, filed as application No. PCT/US02/16082 on May 21, 2002, now Pat. No. 7,273,694.

(60) Provisional application No. 60/292,723, filed on May 21, 2001, provisional application No. 60/293,249, filed on May 24, 2001, provisional application No. 60/293,713, filed on May 25, 2001, provisional application No. 60/294,196, filed on May 29, 2001, provisional application No. 60/295,255, filed on Jun. 1, 2001.

(51) Int. Cl.
| | |
|---|---|
| *C12M 1/00* | (2006.01) |
| *C12M 3/00* | (2006.01) |
| *B01L 3/00* | (2006.01) |
| *C12M 1/32* | (2006.01) |
| *G01N 21/07* | (2006.01) |

(52) U.S. Cl.
CPC .............. *B01L 3/502* (2013.01); *B01L 3/5021* (2013.01); *C12M 33/06* (2013.01); *B01L 2300/0877* (2013.01); *B01L 2400/0409* (2013.01); *G01N 21/07* (2013.01)

(58) Field of Classification Search
CPC .................... A61L 2/0011; Y10T 436/25375; Y10T 436/25125
USPC ..................................... 435/308.1
See application file for complete search history.

(56) References Cited

U.S. PATENT DOCUMENTS

| | | | |
|---|---|---|---|
| 4,076,170 A * | 2/1978 | Chulay et al. | 494/38 |
| 4,435,293 A * | 3/1984 | Graham et al. | 210/772 |
| 2005/0064579 A1* | 3/2005 | Loskutoff et al. | 435/283.1 |

* cited by examiner

*Primary Examiner* — Michael Hobbs
(74) *Attorney, Agent, or Firm* — Suiter Swantz pc llo

(57) ABSTRACT

A centrifuge layering insert configured for insertion into a centrifuge tube includes a tube having a first open end and a second open end. The centrifuge layering insert also includes a casing having an outer wall, an inner wall, a first open end, and a second substantially closed end. The casing forms an annular space around the tube between the tube first end and the tube second end. The tube has at least a portion of the length extending beyond the first open end of the casing in a direction opposite the second open end of the tube.

3 Claims, 7 Drawing Sheets

SYSTEM FOR SEPARATION OF A SAMPLE

CROSS-REFERENCE TO RELATED APPLICATIONS

The present application is a continuation-in-part application and claims priority under 35 U.S.C. §120 to U.S. patent application Ser. No. 11/827,767 entitled: Method and Apparatus for Reducing Pathogens in a Biological Sample, filed Jul. 13, 2007, which claims priority under 35 10 U.S.C. §121 to U.S. application Ser. No. 10/478,917 entitled: Method and Apparatus for Reducing Pathogens in a Biological Sample filed Nov. 21, 2003, now U.S. Pat. No. 7,273,694 (issued Sep. 25, 2007); which claims priority under 35 U.S.C. §119 to PCT/US02/16082, filed May 21, 2002, which claims priority under 35 U.S.C. §119(e) to U.S. Patent Application No. 60/292,723, filed May 15 21, 2001, U.S. Patent Application No. 60/293,249, filed May 24, 2001; U.S. Patent Application No. 60/293,713, filed May 25, 2001; U.S. Patent Application No. 60/294,196, filed May 29, 2001; and U.S. Patent Application No. 60/295,255, filed Jun. 1, 2001, which are herein incorporated by reference in their entirety.

FIELD

The present disclosure generally relates to the field of contamination of biological samples, and particularly to a system and method for separation of materials in a biological sample.

BACKGROUND

Maintaining separation of a treated biological sample from the substances used to treat the sample may be desirable. For instance, a great risk exists concerning transmission of pathogenic agents in biological samples. Treatment of biological samples which potentially contain pathogenic agents may pose a risk to individuals performing the treatment. Additionally, during and after treatment, the sample must remain separated from any potentially contaminated portions to avoid recontamination.

Additionally, it may be desirable to separate portions of a biological sample from other portions of the biological sample. In particular, with a biological sample such as seminal fluid, it may be desirable to separate the more motile sperm from the rest of the sample which may include less motile sperm and to maintain that separation to provide a biological sample with a higher concentration of motile sperm. While density gradients may be used to separate substances, creating and maintaining the density gradient may be difficult, with significant opportunities to mix layers prior to and during use. Such opportunities to mix may be undesirable when dealing with potentially contaminated samples, or when a specific concentration of a treated sample is desired.

SUMMARY

A centrifuge layering insert configured for insertion into a centrifuge tube includes a tube having a first open end and a second open end. The tube has a length between 75 and 95 percent of the centrifuge tube and an outside diameter of between 30 and 60 percent of an inside diameter of the centrifuge tube. The centrifuge layering insert also includes a casing having an outer wall, an inner wall, a first open end, and a second substantially closed end. The second substantially closed end forms an opening through the outer wall and the inner wall. The casing forms an annular space around the tube between the tube first end and the tube second end. At least a portion of the casing has an outer diameter of between 75 and 100 percent of the inside diameter of the centrifuge tube. The casing includes means for slidable removable retention within the centrifuge tube. The casing has an outer diameter at the first open end of greater than approximately 100 percent of the inside diameter of the centrifuge tube. The tube has at least a portion of the length extending beyond the first open end of the casing in a direction opposite the second open end of the tube.

A system for separation of a biological sample includes a centrifuge tube configured for use in a centrifuge apparatus. The centrifuge tube includes a first open end and a second closed end. The system also includes a centrifuge layering insert configured for insertion into a centrifuge tube. The centrifuge layering insert includes a tube having a first open end and a second open end. The tube has a length between 75 and 95 percent of the centrifuge tube and an outside diameter of between 30 and 60 percent of an inside diameter of the centrifuge tube. The centrifuge layering insert also includes a casing having an outer wall, an inner wall, a first open end, and a second substantially closed end. The second substantially closed end forms an opening through the outer wall and the inner wall. The casing forms an annular space around the tube between the tube first end and the tube second end. The casing has an outer diameter of between 75 and 100 percent of the inside diameter of the centrifuge tube. The casing has an outer diameter at the first open end of greater than approximately 100 percent of the inside diameter of the centrifuge tube. The tube has at least a portion of the length extending beyond the first open end of the casing in a direction opposite the second open end of the tube.

A centrifuge layering insert configured for insertion into a centrifuge tube includes a tube having a first open end and a second open end. The tube has a length between 75 and 95 percent of the centrifuge tube and an outside diameter of between 30 and 60 percent of an inside diameter of the centrifuge tube. The centrifuge layering insert also includes a casing having an outer wall, an inner wall, a first open end, and a second substantially closed end. The second substantially closed end forms an opening through the outer wall and the inner wall. The casing forms an annular space around the tube between the tube first end and the tube second end. The casing has an outer diameter of between 75 and 100 percent of the inside diameter of the centrifuge tube. The casing has an outer diameter at the first open end of greater than approximately 100 percent of the inside diameter of the centrifuge tube. The tube has at least a portion of the length extending beyond the first open end of the casing in a direction opposite the second open end of the tube.

It is to be understood that both the foregoing general description and the following detailed description are exemplary and explanatory only and are not necessarily restrictive of the disclosure as claimed. The accompanying drawings, which are incorporated in and constitute a part of the specification, illustrate an embodiment of the disclosure and together with the general description, serve to explain the principles of the disclosure.

BRIEF DESCRIPTION OF THE DRAWINGS

The numerous advantages of the present disclosure may be better understood by those skilled in the art by reference to the accompanying figures in which.

DETAILED DESCRIPTION

Figure 1:
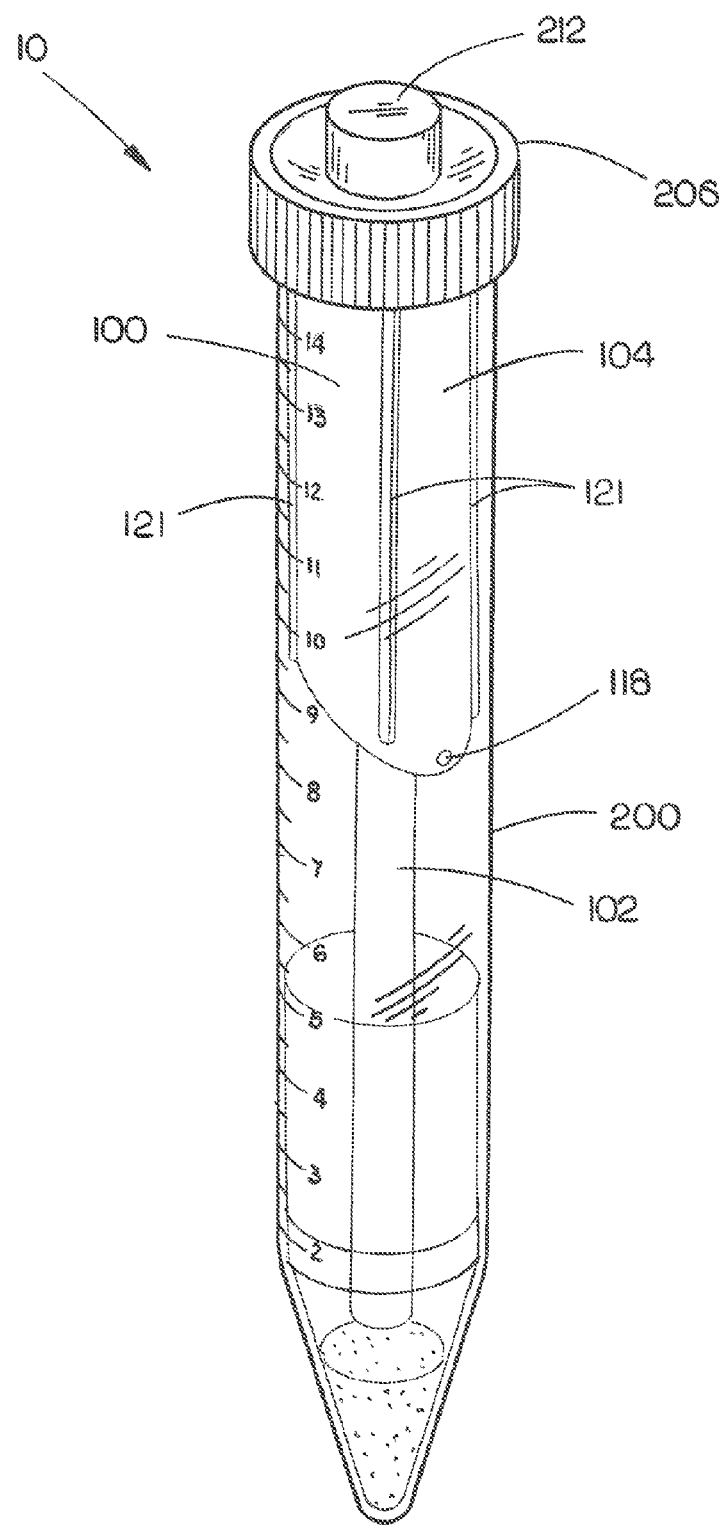
FIG. 1 is an isometric view of a separation system in accordance with an embodiment of the present disclosure, including a density gradient and a biological sample.

Reference will now be made in detail to the presently preferred embodiments of the present disclosure, examples of which are illustrated in the accompanying drawings.

Referring generally now to FIGS. 1-9B, embodiments of a separation system 10 are illustrated. The separation system 10 may include a centrifuge layering insert 100, a centrifuge tube 200, and an aspiration device 300. The centrifuge layering insert 100 may be configured for insertion into the centrifuge tube 200 for facilitating the introduction and layering of a sample and/or sample treatment substances into the centrifuge tube 200, and the aspiration device 300 may be configured for removing a treated sample from the centrifuge tube 200, all of which will be discussed further below.

The centrifuge layering insert 100 may include a tube 102 and a casing 104. The tube 102 may include a first open end 106 and a second open end 108. The casing 104 may be configured to provide an annular space 110 around the tube, such that a sample may be inserted into the casing 104 between the tube 102 and an inner wall 112a of the casing 104. The casing 104 may include the inner wall 112a, an outer wall 112b, a first open end 114, and a second substantially closed end 116, where the casing 104 forms the annular space 110 around the tube 102 between the tube first end 106 and the tube second end 108. For instance, in one embodiment, the casing 104 may provide a substantially enclosed portion around the tube 104 beginning at approximately three percent to ten percent of the length of the tube 102 from the first open end 106 and ending between approximately 30 percent to approximately 75 percent of the length of the tube 102. The length, shape, etc. of the casing 104 may vary depending on the volume/amount of sample to be processed by the centrifuge layering insert 100.

The second substantially closed end 116 of the casing 104 may form an opening 118 through and between the inner wall 112a and the outer wall 112b. The opening 118 may provide an outlet for a sample within the casing 104 to exit the casing 104 at or near the second substantially closed end 116. In a particular embodiment, the second substantially closed end 116 of the casing 104 may be of a slanted or angled configuration, such as that shown in FIG. 4, with the opening 118 located near the bottom of the second substantially closed end 116 (i.e., furthest away from the first open end 114 of the casing 104). Such a configuration may facilitate in passage of sample from inside the casing 104 to outside the casing 104 (e.g., into centrifuge tube 200). The size of the casing 104 and of the opening 118 may determine the volume of sample that the centrifuge layering insert 100 may process, and the residence time of the sample within the casing 104. For instance, by reducing the size of opening 118, the flow rate of the sample leaving the centrifuge layering insert 100 via opening 118 may decrease, thereby reducing the total volume that the centrifuge layering insert 100 may process in a given time period. In a particular embodiment, the opening 118 is between approximately 0.1 millimeters and 10 millimeters, the value of which may depend upon the viscosity of the sample and the volume of centrifuge tube 200 into which the centrifuge layering insert 100 is configured to be inserted. For example, for a centrifuge tube 200 with a volume of approximately 15 milliliters, the opening 118 may be approximately 1 millimeter.

The casing 104 and the tube 102 may be fixedly or removeably attached to each other. For instance, in one embodiment, the tube 102 is integrally related to the casing 104 to provide a substantially sealed environment which is substantially separated from the centrifuge tube 200 when the centrifuge layering insert 100 is inserted into the centrifuge tube 200. The casing 104 may also include a lip portion 120 which may be configured for retaining at least a portion of the centrifuge layering insert 100 above the top edge 202 of the centrifuge tube 200. For example, the lip portion 120 may be a portion of the casing 104 having an outer diameter at the first open end 114 of greater than approximately 100 percent of the inside diameter of the centrifuge tube 200. Thus, when the centrifuge layering insert 100 is inserted into the centrifuge tube 200, the lip portion 120 may prevent at least a portion of the centrifuge layering insert 100 from being completely inserted into the centrifuge tube 200, particularly when centrifuge layering insert 100 has a length less than the length of the centrifuge tube 200. Additionally, the lip portion may serve to substantially cover the open end of the centrifuge tube 200 to prevent substances from entering the centrifuge tube 200 unless the substance passes through opening 118 of the casing 104. In one embodiment, the tube 102 of the centrifuge layering insert 100 has a length of between approximately 75 percent and 95 percent of the length of the centrifuge tube 200 into which the centrifuge layering insert 100 is configured to be inserted. By including a length of the tube 102 less than the length of the centrifuge tube 200, the centrifuge layering insert 100 may provide a gap at the bottom end of the centrifuge tube 200 in which a sample pellet may form during centrifugation. Retaining the tube 102 of the centrifuge layering insert 100 above the sample pellet may ensure more complete removal of the sample pellet through the tube 102, as will be further described below. However, depending on the sample type and the substances used to treat the sample, the tube may reach the bottom end of the centrifuge tube 200 in some instances.

The casing may also include means for slidable removable retention within the centrifuge tube 200. The means for slidable removable retention may extend from the outer wall 112b of the casing 104 and may be configured to contact the inside of the centrifuge tube 200, such as for stabilization of the centrifuge layering insert 100 within the centrifuge tube 200. The means for slidable removable retention may include retention member 121. The retention member 121 may be configured to reduce or prevent rotational and/or lateral movement of the centrifuge layering insert 100 within the centrifuge tube 200. For instance, when the outer diameter of the casing 104 is less than the inner diameter of the centrifuge tube 200, the retention member 121 may contact the inner wall of the centrifuge tube 200, and may brace the centrifuge layering insert 100 against the centrifuge tube. The retention member 121 may protrude from the surface to contact at least a portion of the centrifuge tube wall (as displayed in FIGS. 1-3 and 5-9B), or, in another embodiment, may be a recess configured to receive a protrusion from the centrifuge tube wall. For instance, retention member 121 may be a ridge extending at least partially in a longitudinal direction on the outer wall 112b of the casing 104 between the first open end 114 and the second substantially closed end 116. The centrifuge layering insert 100 may further include a plurality of retention members 121 spaced apart on the outer wall 112b of the casing 104. Additionally, where the outer diameter of the casing 104 is approximately equal to the inner diameter of the centrifuge tube 200, the means for slidable removable retention may be the outer wall 112b of the casing 104, which may contact at least a portion of the centrifuge tube wall.

The tube 102 of the centrifuge layering insert 100 may include a raised portion 122 which may extend beyond the lip portion 120 of the casing 104 in a direction opposite the second open end 108 of the tube 102. For instance, when the centrifuge layering insert 100 is in an upright position, such as that shown in FIGS. 1-9B, the raised portion 122 may be positioned above the casing 104 adjacent the lip portion 120. The raised portion 122 may have a length of between approximately three percent and ten percent of the entire length of the tube 102. The percentage of the entire length of the tube 102 may vary depending on the length of the centrifuge tube 200 into which the centrifuge layering insert 100 is configured to be inserted, and depending on the desired total length of the tube 102. In one embodiment, the raised portion 122 is approximately five percent of the entire length of the tube 102. Thus, when the centrifuge layering insert 100 is completely inserted into the centrifuge tube 200 (e.g., lip portion 120 substantially prevents further insertion into the centrifuge tube 200), the raised portion 122 is above the top edge 202 of the centrifuge tube 200.

Figure 5:
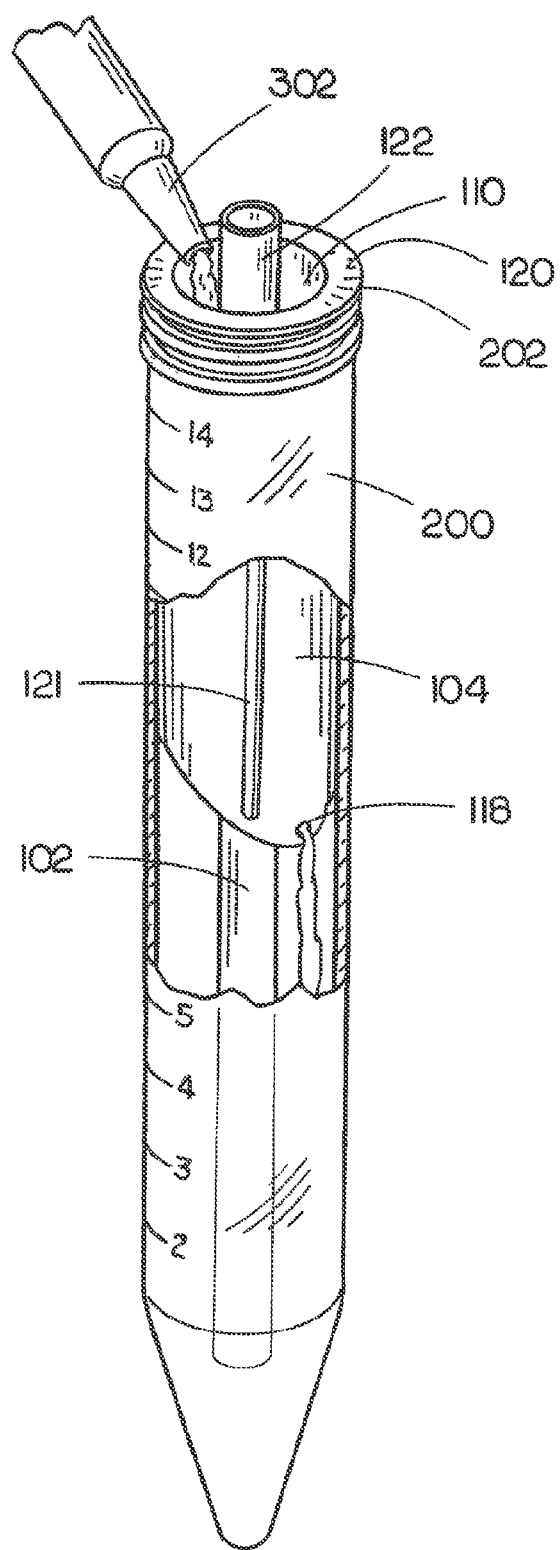
FIG. 5 is a partial cross-sectional isometric view of the separation system shown in FIG. 1, including application of a biological sample to the separation system.
Figure 6:
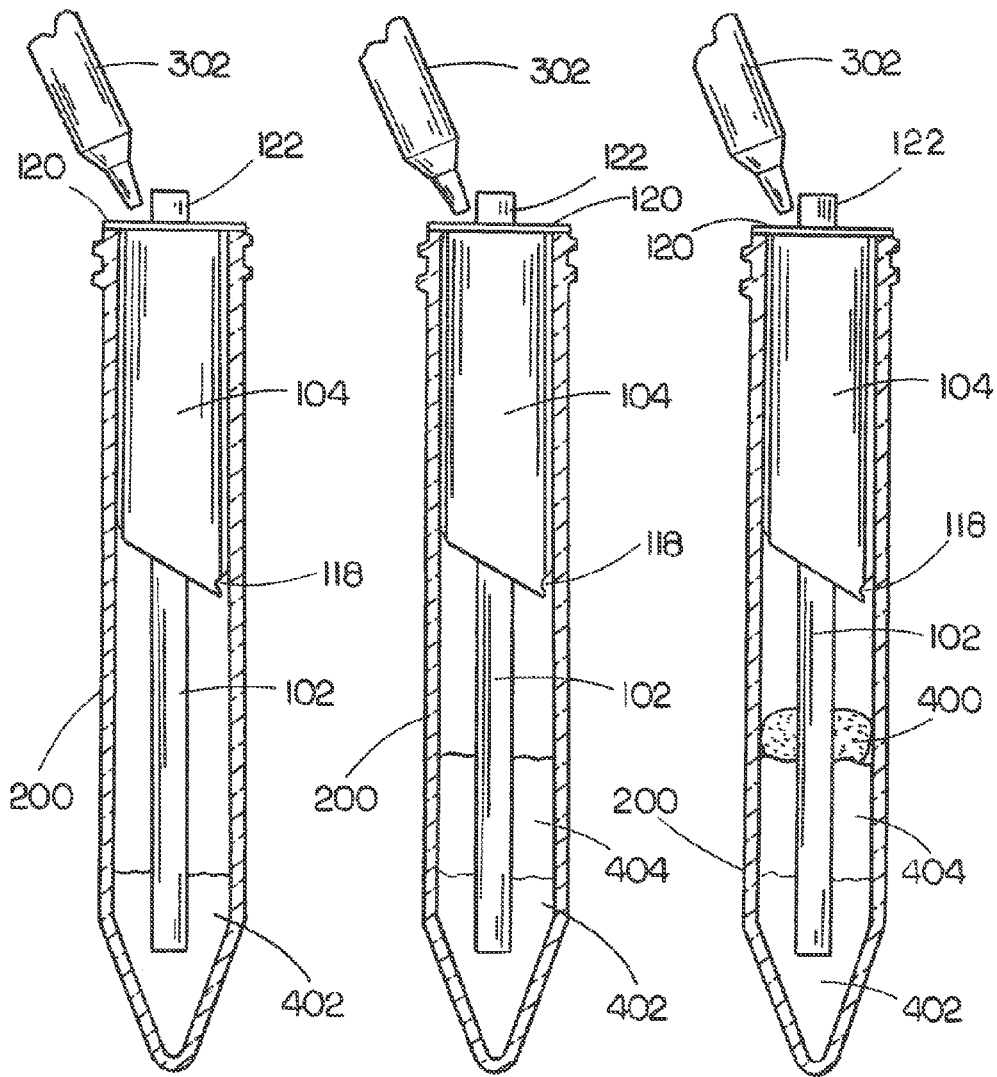
FIGS. 6A-6C are partial cross-sectional side views of the separation system shown in FIG. 1, including various layers of biological sample and/or density gradient.

As shown in FIG. 5, the raised portion 122 may provide a boundary between the annular space 110 defined by the casing 104 and an aspiration channel 124 defined by an interior wall 126 of the tube 102. This boundary acts as a physical separation between the annular space 110 and the aspiration channel 124 such that an attempt by a user to successfully insert a substance, such as a sample, into the annular space 110 rather than into the aspiration channel 124 is improved. For instance, when the separation system 10 is used in conjunction with contaminated or potentially contaminated substances, it may be preferable to avoid inserting any portion of the pre-treated sample into the aspiration channel 124, as the aspiration device 300 will enter the aspiration channel 124 to remove an uncontaminated sample through the aspiration channel 124 after treatment. The annular space 110 may vary depending on the cross-sectional area occupied by the tube 102 and by the casing 104. By reducing the size of the cross-sectional area occupied by the tube 102, the annular space 110 may be relatively larger, providing a larger area into which a substance may be introduced to the casing 104. In a particular embodiment, the outside diameter of the tube 102 is formed by an exterior wall 127. The outside diameter of the tube 102 may be between approximately 30 percent and 60 percent of an inside diameter of the centrifuge tube 200. Further, by avoiding insertion of any portion of the pre-treated sample into the aspiration channel 124, the risk of recontamination of the sample is substantially reduced. Again, by reducing the size of the cross-sectional area occupied by the tube 102, the risk of introducing a pre-treated sample into the aspiration channel 124 is reduced.

By inserting a substance into the annular space 110 of the casing 104, the substance may travel to the second substantially closed end 116 of the casing 104, where the substance may then exit the casing via opening 118. The size of opening 118 may provide a residence time within the casing 104, and may allow for controlled decanting of the substance out of the casing 104 and into contact with an inner wall of the centrifuge tube 200. Thus, the centrifuge layering insert 100 may work in conjunction with the centrifuge tube 200 to provide a separation system 10 which facilitates accurate and controlled decanting of substances into the centrifuge tube. This may be particularly important in creating density gradients, which may be prone to inadvertent mixing or incomplete separation due to hasty preparation.

FIGS. 6A-6C show a device 302 being used to introduce substances to the separation system 10. In particular, the device 302 may introduce the substances into the annular space 110 of the casing 104, such that the substances enter the casing 104, rather than the aspiration channel 124 of the tube 102. In particular, the raised portion 122 may be seen above the lip portion 120 of the casing 104, which provides a visual and physical indication of the boundary between the annular space 110 and the aspiration channel 124.

Figure 2:
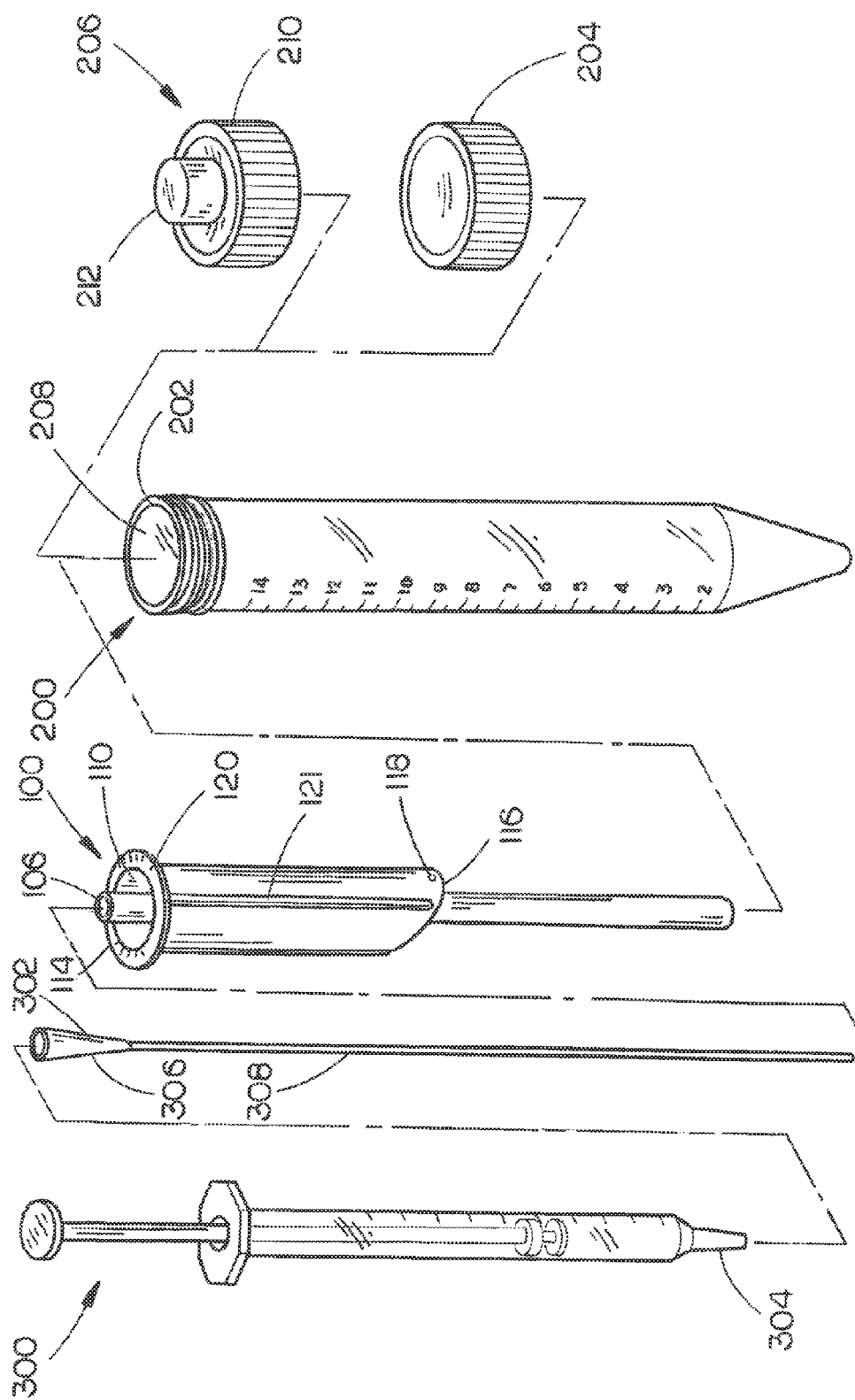
FIG. 2 is an exploded isometric view of the separation system shown in FIG. 1, including a plurality of caps.
Figure 3:
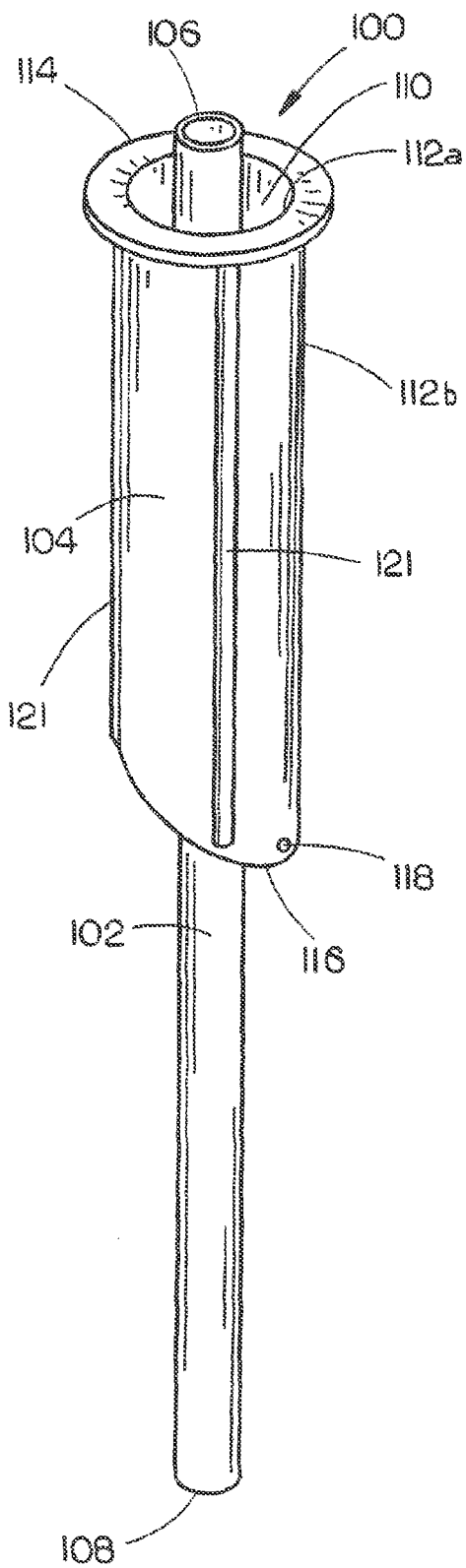
FIG. 3 is an isometric view of a layering device of the separation system shown in FIG. 1.
Figure 4:
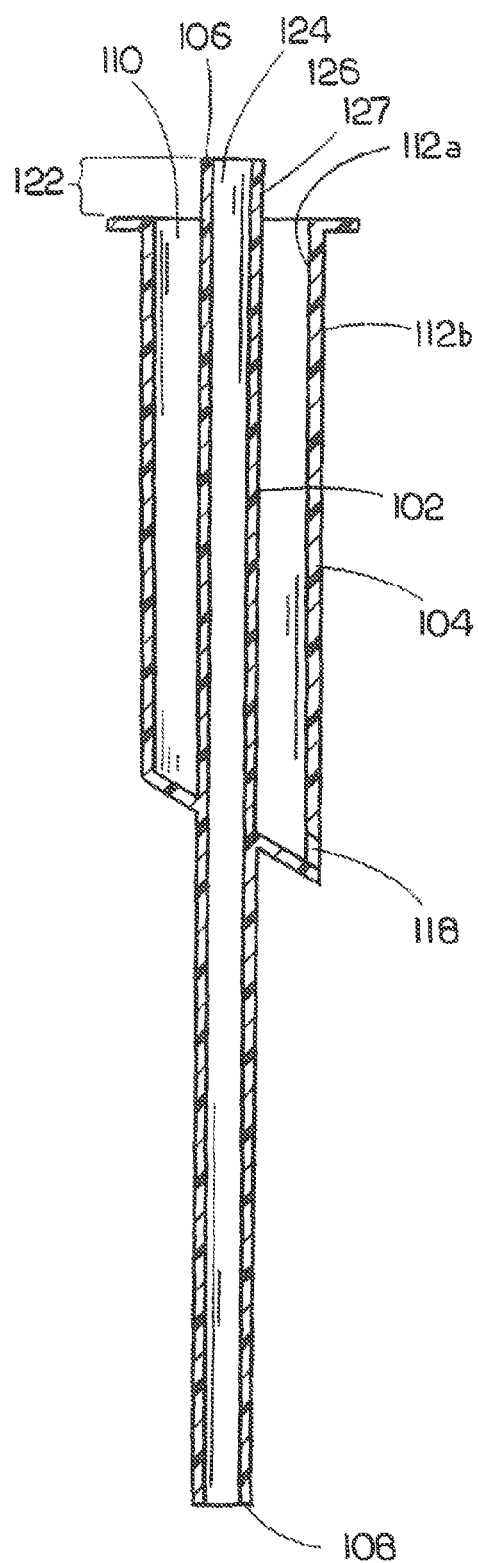
FIG. 4 is a cross-sectional view of the layering device shown in FIG. 3.
Figure 7:
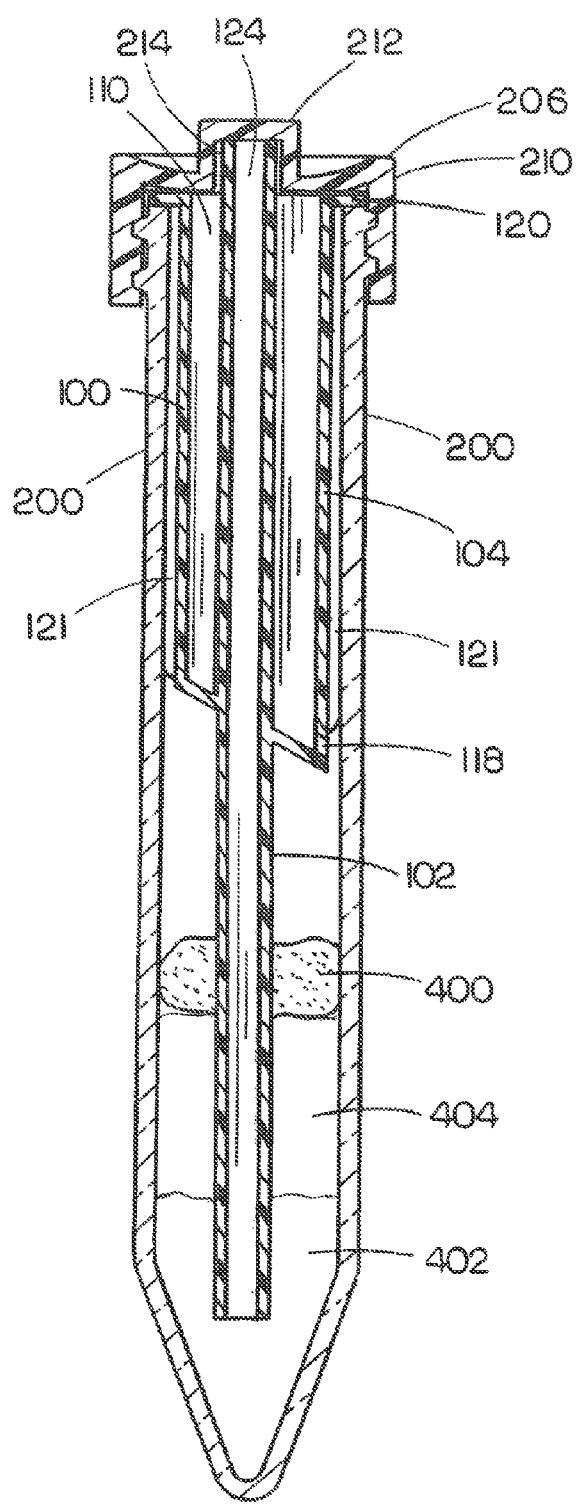
FIG. 7 is a cross-sectional side view of the separation system shown in FIG. 1, including a two-layered density gradient and a biological sample.

The handling of biological and chemical samples may benefit from or require a sealed system during sample treatment. For instance, a centrifuge may be utilized to rotate the centrifuge tube 200 as a part of the treatment of a sample. As seen in FIG. 2, a centrifuge cap 204 typically may be utilized with centrifuge tube 200. For instance, centrifuge cap 204 may couple with the centrifuge tube 200 via a screw mechanism, but other means of securing centrifuge cap 204 with centrifuge tube 200 may be utilized. However, centrifuge cap 204 may not fully couple with the centrifuge tube 200 when centrifuge layering insert 100 is utilized, due to the raised portion 122. For example, when the centrifuge layering insert 100 is fully inserted into the centrifuge tube 200, such that the lip portion 120 is in contact with the top edge 202 of the centrifuge tube 200, the raised portion 122 may extend beyond the top edge 202 of the centrifuge tube 200. Such a configuration may result in the raised portion 122 contacting a portion of the centrifuge cap 204, interfering with the ability of the centrifuge cap 204 to secure to and couple with the centrifuge tube 200. As seen in FIGS. 1, 2, 7, and 8, the separation system 10 may further include a centrifuge tube cap 206 which may be removably attachable to an open end 208 of the centrifuge tube 200. The centrifuge tube cap 206 includes a body portion 210 and a protrusion 212 extending from the body portion 210. The protrusion 212 forming an elongated channel 214 on the inner portion of the centrifuge tube cap 206 (as seen in FIG. 7). The protrusion 212 is configured to align with the raised portion 122 of the centrifuge layering insert 100 when the centrifuge layering insert 100 is inserted into the centrifuge tube 200 and the centrifuge tube cap 206 is secured to the centrifuge tube 200. The elongated channel 214 formed by the protrusion 212 generally may have a length of greater than or equal to the length of the raised portion 122. For example, the elongated channel 214 may have a length of between approximately three percent and ten percent of the length of the tube 102. With such a configuration, the centrifuge layering insert 100 may be fully inserted into the centrifuge tube 200 and the centrifuge tube cap 206 may fully secure to the open end 208 of the centrifuge tube 200, without substantial interference by the raised portion 122 of the centrifuge layering insert 100.

The length of the raised portion 122 and of the elongated channel 214 formed by the protrusion 212 may be selected to provide the boundary between the annular space 110 of the casing 104 and the aspiration channel 124 of the tube 102, as described above. The length of the raised portion 122 and of the elongated channel 214 formed by the protrusion 212 also may be selected to conform to space associated with use of a centrifuge.

For instance, a centrifuge may include limited space when including multiple centrifuge tubes in close proximity. The length of the raised portion 122 and of the elongated channel 214 formed by the protrusion 212 may be selected to avoid substantial contact between centrifuge tubes 200 adjacent and/or across from one another when placed in the centrifuge tube. By limiting the interaction between multiple centrifuge tubes 200, more samples may be treated simultaneously, thereby contributing to the efficiency of treatment of multiple samples.

Referring now to FIGS. 6A-9B, an example of the use of the separation system 10 is shown. In the embodiments shown in FIGS. 6A-9B, a sample 400 is treated by using a density gradient, coupled with centrifugation. The density gradient may include a first layer 402 and a second layer 404. The first layer 402 may comprise a substance having a higher density relative to the second layer 404. For example, the first layer 402 and the second layer 404 may comprise a silica-based substance utilized to provide resistance against a seminal fluid sample 400 to separate motile sperm from non-motile sperm. The separation system may also incorporate enzymatic solution(s) and enzyme inactivator(s) to decontaminate the sample 400 from viruses, bacteria, and the like, such as described in U.S. Pat. No. 7,405,036 to Loskutoff et al., which is hereby incorporated by reference in its entirety.

FIG. 6A shows the centrifuge layering insert 100 fully inserted into the centrifuge tube 200, with the lip portion 120 contacting the top edge 202 of the centrifuge tube 200, and with the raised portion 122 above the top edge 202 of the centrifuge tube 200. Device 302 introduces a substance into the annular space 110 of the casing 104, which, when decanted through opening 118, forms the first layer 402 in the bottom of centrifuge tube 200. In FIG. 6B, the device 302 introduced a substance into the annular space 110 of the casing 104, which, when decanted through opening 118, forms the second layer 404 on top of the first layer 402. For instance, the first layer 402 and the second layer 404 may separate due to a density differential. When utilizing a silica-based substance for the first layer 402 and the second layer 404, a separation may be difficult to discern based on the clarity/turbidity of the solutions. However, the centrifuge layering insert 100 may prevent substantial mixing of the first layer 402 and the second layer 404 due to the decanting of the solutions through opening 118. Therefore, the separation of the layers may be obtained without the use of dyes or the like used to differentiate the layering. In FIG. 6C, the device 302 introduced a sample 400 into the annular space 110 of the casing 104, which, when decanted through opening 118, forms a sample layer 400 on top of the second layer 402. At this point, the sample may be ready for treatment, which in this example, includes centrifugation.

Figure 8:
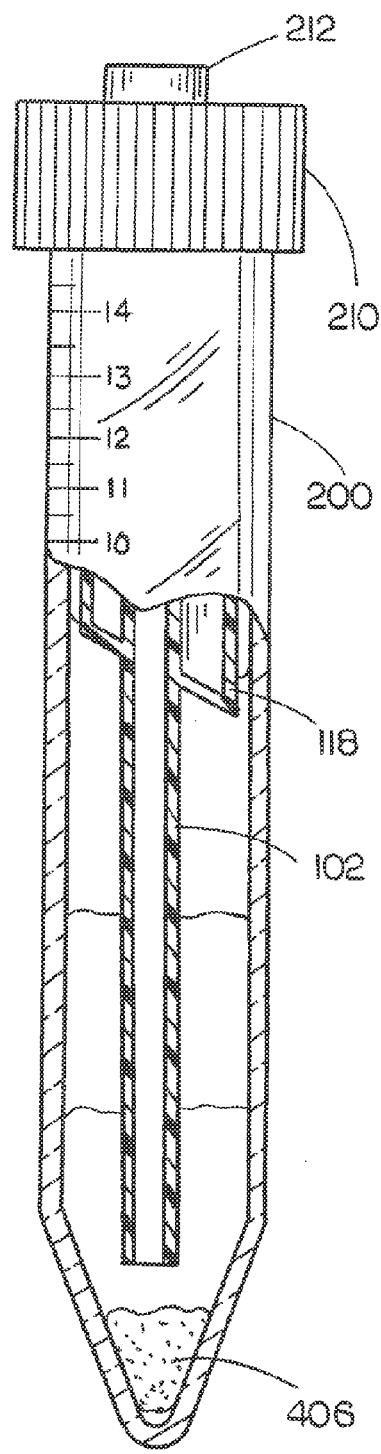
FIG. 8 is a partial cross-sectional side view of the separation system shown in FIG. 7, with the two-layered density gradient and the biological sample after centrifugation.

In FIG. 7, the centrifuge tube cap 206 has been secured to the centrifuge tube 200, in preparation for centrifugation. As can be seen, the elongated channel 214 formed by the protrusion 212 of the centrifuge tube cap 206 aligns with the tube 102 of the centrifuge layering insert 100, such that the raised portion 122 fits into the elongated channel 214. Thus, a compact configuration may be achieved which may enable retention of the centrifuge layering insert 100 within the centrifuge tube 200 during centrifugation, such that the centrifuge layering insert 100 may be utilized to remove a treated sample pellet 406 (FIG. 8). In FIG. 8, the separation system 10 has been centrifuged, resulting in a treated sample pellet 406 at the bottom of the centrifuge tube 200. In the example of seminal fluid as the sample 400, the treated sample pellet 406 may include a relatively high concentration of motile sperm, whereas less motile sperm may have been separated from the sample 400 due to interaction with the first layer 402 and the second layer 404. The treated sample pellet 406 may then be ready for extraction from the centrifuge tube.

Figure 9A:
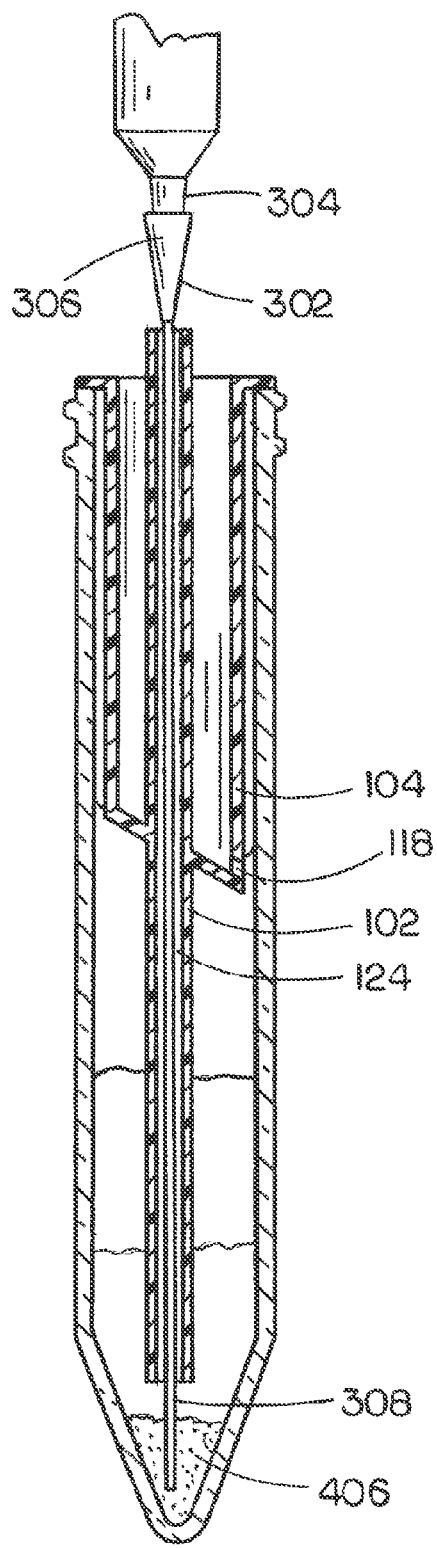
FIGS. 9A and 9B are partial cross-sectional side views of the separation system shown in FIG. 7, including insertion of a removal device into the separation system and removal of a sample pellet.

In FIG. 9A, the aspiration device 300 may be configured to remove the treated sample pellet 406 from the bottom end of the centrifuge tube 200. As described above, the tube 102 of the centrifuge layering insert 100 may include an aspiration channel 124 within the tube 102 through which the treated sample pellet may pass. The walls of the tube 102 may physically separate the aspiration channel 124 from the casing 104 and from the centrifuge tube 200, providing an environment from which to remove the treated sample pellet 406.

Figure 9B:
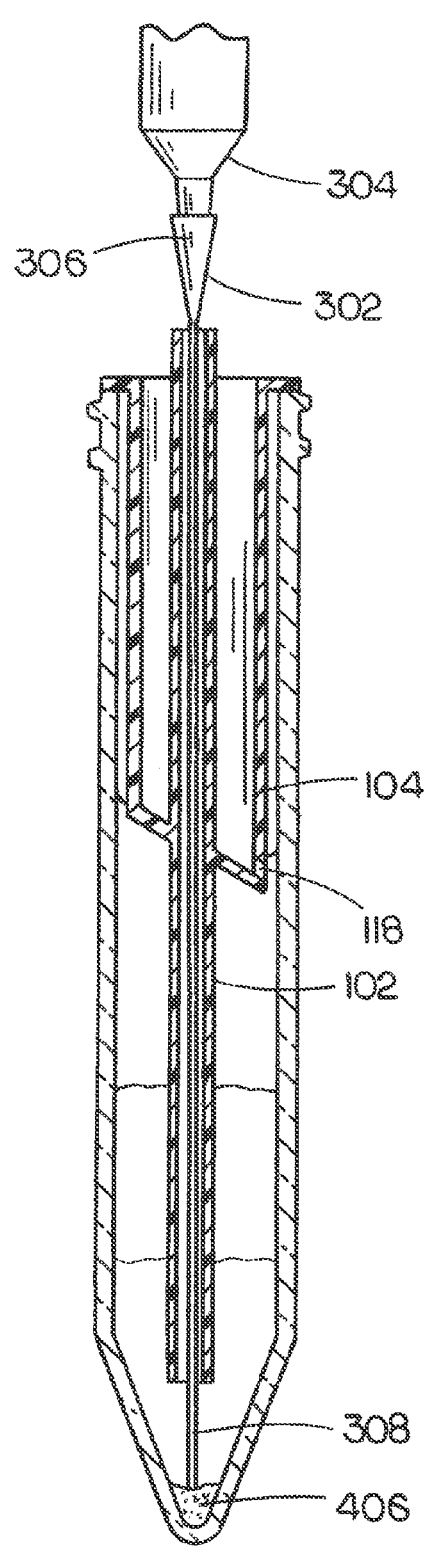

As shown in FIGS. 2, 9A, and 9B, the aspiration device 300 may be a syringe, which may include an extension device 302 removably coupled to an end 304 of the aspiration device 300. As shown in FIG. 9B, the extension device 302 may be configured to pass within the aspiration channel 124 in order to remove at least a portion of the treated sample pellet 406 from the bottom of the centrifuge tube 200. In this manner, the extension device 302 may avoid substantial contact with the first layer 402 and the second layer 404, which may be contaminated after treatment of the sample 400. The extension device 302 may include a coupling portion 306, which may be configured to attach to and couple with the end 304 of the aspiration device 300. The extension device 302 may also include an insertion portion 308 configured for insertion into the aspiration channel 124. In a particular embodiment, the coupling portion 306 and the insertion portion 308 are fixedly attached, such as by fusing them together, or by being constructed from a single material. Such a configuration may reduce the potential for disconnection of the coupling portion 306 and the insertion portion 308 when removing a sample. The extension device 302 may have a length configured to interact with the treated sample pellet 406 at the bottom of the centrifuge tube 200. For instance, the extension device 302 may have a length at least equal to the length of tube 102. The extension device 302 may have a length sufficient to reach the bottom of the centrifuge tube 200 when the extension device 302 is inserted into the aspiration channel 124 with the centrifuge layering insert 100 fully inserted into the centrifuge tube 200.

It is believed that the present disclosure and many of its attendant advantages will be understood by the foregoing description, and it will be apparent that various changes may be made in the form, construction and arrangement of the components thereof without departing from the scope and spirit of the disclosure or without sacrificing all of its material advantages. The form herein before described being merely an explanatory embodiment thereof, it is the intention of the following claims to encompass and include such changes.

What is claimed is:

1. A centrifuge layering insert configured for insertion into a centrifuge tube during centrifugation, comprising:
    a tube having a first open end and a second open end, the tube having a length between 75 and 95 percent of the centrifuge tube and an outside diameter of between 30 and 60 percent of an inside diameter of the centrifuge tube; and a casing having an outer wall, an inner wall, a first open end, and a second substantially closed end, the second substantially closed end forming an opening through the outer wall and the inner wall, the casing forming an annular space around the tube between the tube first end and the tube second end for receiving a sample, at least a portion of the casing having an outer diameter of between 75 and 100 percent of the inside diameter of the centrifuge tube, the casing including a plurality of longitudinal retention grooves defined by the outer wall and configured to engage longitudinal protrusions disposed on an inner wall of the centrifuge tube to prevent rotation of the centrifuge layering insert, the casing having an outer diameter at the first open end of greater than approximately 100 percent of the inside diameter of the centrifuge tube, the tube having at least a portion of the length extending beyond the first open end of the casing in a direction opposite the second open end of the tube for preventing contamination of an aspiration channel by the sample, wherein the portion of the length of the tube extending beyond the first open end of the casing is configured to align with an elongated channel of a centrifuge tube cap when the centrifuge layering insert is inserted into the centrifuge tube and the centrifuge tube cap is attached to an open end of the centrifuge tube.

2. The centrifuge layering insert of claim 1, wherein the portion of the length extending beyond the first open end of the casing is between approximately three percent and ten percent of the length of the tube.

3. The centrifuge layering insert of claim 1, wherein the opening formed by the second substantially closed end of the casing is between approximately 0.1 millimeters and 10 millimeters.

* * * * *